United States Patent [19]
Suh et al.

[11] Patent Number: 4,555,508
[45] Date of Patent: Nov. 26, 1985

[54] ANTIHYPERTENSIVE SPIRO-CYCLIC COMPOUNDS

[75] Inventors: John T. Suh, Greenwich, Conn.; John R. Regan, Mamaroneck, N.Y.; John J. Piwinski, Parsippany, N.J.; Paul Menard, Tuckahoe; Howard Jones, Ossining, both of N.Y.

[73] Assignee: USV Pharmaceutical Corp., Tarrytown, N.Y.

[21] Appl. No.: 585,697

[22] Filed: Mar. 2, 1984

[51] Int. Cl.[4] .................. A61K 37/00; C07D 279/00; C07C 103/52
[52] U.S. Cl. .................................. 514/211; 514/212; 514/218; 514/222; 544/6; 260/243.3; 260/112.5 R
[58] Field of Search ............ 260/112.5 R, 243.3; 424/177; 544/6; 514/212, 211, 218, 222

[56] References Cited
FOREIGN PATENT DOCUMENTS
0050800 5/1982 European Pat. Off. ..... 260/112.5 R Primary Examiner—Delbert R. Phillips

[57] ABSTRACT

Compounds having the general structure

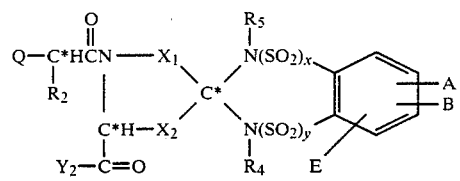

and their pharmaceutically acceptable salts, wherein the substituents are defined herein, which exhibit antihypertensive activity.

23 Claims, No Drawings

ANTIHYPERTENSIVE SPIRO-CYCLIC COMPOUNDS

BACKGROUND OF THE INVENTION

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula (1)

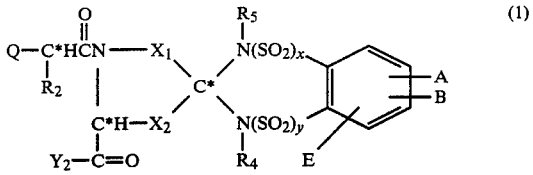

and their pharmaceutically acceptable acid addition, alkali metal, and alkaline earth metal salts, wherein Q is $Y_1$—C(O)—C*H($R_1$)—NH—, —$NH_2$, $R_1$—C(O)—S—(C*H($R_1$))$_{0-1}$—, or HS—(C*H($R_1$))$_{0-1}$—;

$Y_1$ and $Y_2$ are independently —OH, —OR, or —$NR_1R_2$;

one of x and y is 1 and the other is 0;

R, $R_1$, $R_2$, $R_4$ and $R_5$ are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

A, B and E are independently H, halogen, —OH, —OR, —$CF_3$, —$NR_1R_2$, —C(O)$Y_1$, —$SO_2R$, or —$SO_2NR_1R_2$; provided that at least two of A, B and E are not H;

$X_1$ is —(CH$_2$)$_a$—, —(CH$_2$)$_b$S(CH$_2$)$_c$—, —(CH$_2$)$_b$C(O)(CH$_2$)$_c$—, or —(CH$_2$)$_b$CH(R$_3$)(CH$_2$)$_c$—;

$X_2$ is —(CH$_2$)$_d$—, —(CH$_2$)$_e$S(CH$_2$)$_f$—, —(CH$_2$)$_e$C(O)(CH$_2$)$_f$—, or —(CH$_2$)$_e$CH(R$_3$)(CH$_2$)$_f$—;

provided that a and d are each 0-4; b c, e, and f are each 0-3; (a+d) is 2-4; (a+e+f) is 1-3; (b+c+d) is 1-3; and (b+c+e+f) is 0-2; and $R_3$ is —OH, phenyl, or an alkyl or alkoxy group having up to 6 carbon atoms;

wherein the alkyl, cycloalkyl, aryl, and fused aryl-cycloalkyl groups may carry substituents selected from the group consisting of alkoxy with 1 to 6 carbon atoms, alkyl with 1 to 6 carbon atoms, —$CF_3$, —OH, —SH, halogen, —$NO_2$, and —COOR.

DETAILED DESCRIPTION OF THE INVENTION

Preferred substituents within the scope of the present invention include those wherein $Y_1$ and $Y_2$ are independently hydroxy or alkoxy containing up to 8 carbon atoms;

$R_1$ is H; alkyl having 1 to 8 carbon atoms; phenylalkyl wherein the alkyl has 1 to 4 carbon atoms, and more preferably phenethyl; or indanyl, e.g. 2-indanyl;

$R_2$ is H; alkyl having 1 to 8 carbon atoms; or an alkyl group having 1 to 8 carbon atoms, which is substituted with amino or an amino derivative such as —NH—C($NH_2$)=NH, or

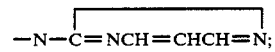

and $R_2$ is and more preferably $NH_2(CH_2)_4$—.

A is —$NH_2$; —OH; phenoxy; alkoxy having up to 6 carbon atoms; —$SO_2NR_1R_2$ wherein $R_1$ and $R_2$ are hydrogen, methyl, or $C_{2-3}$ alkyl, more preferably both hydrogen;

B is halogen, and more preferably chloro; or —$CF_3$; and E is halogen or hydrogen.

The ring formed by $X_1$, $X_2$, and the atoms to which they are connected, contains a total of 5, 6 or 7 atoms. In a most preferred embodiment, both $X_1$ and $X_2$ are —$CH_2$—, thereby forming a proline ring. $X_1$ or $X_2$ can be substituted with an $R_3$ group which is preferably —OH or alkyl containing 1 to 6 carbon atoms. Preferred substituents for $R_4$ and $R_5$ are —H, or alkyl having 1 to 2 carbon atoms, The alkyl groups include straight-chained and branched groups, including methyl, ethyl, propyl, isopropyl, butyl, isobutyl, tert-butyl, amyl, iso-amyl, hexyl, and the like. By "halogen" is meant chloro, bromo, iodo, and fluoro.

Preferred substituents for $R_1$ and/or $R_2$ also include cycloalkyl groups, aryl groups, heterocyclic groups, and fused aryl-cycloalkyl groups, as defined herein, any of which can be connected to the main chain of the molecule (1) directly or through an alkylene bridge —(CH$_2$)$_n$—wherein n is 1 to 6. The preferred cycloalkyl groups include cyclopropyl, cyclobutyl, cyclopentyl, cyclohexyl, cycloheptyl, adamantyl, or norbornyl. The preferred aryl and fused aryl-cycloalkyl groups include phenyl, indolyl, indolino, indanyl, naphthyl, tetrahydronaphthyl, and decahydronaphthyl. Preferred heterocyclic groups include pyridyl, quinolyl, isoquinolyl, tetrahydroquinolyl, tetrahydroisoquinolyl, decahydroquinolyl, decahydroisoquinolyl, pyrrolidyl, pyrrolyl, morpholinyl, furyl, tetrahydrofuryl, furfuryl, benzimidazolyl, thienyl, and imidazolyl. Preferred arylalkyl substituents include benzyl and phenethyl. Preferred substituents on the alkyl, cycloalkyl, aryl, and fused aryl-cycloalkyl substituents include alkyl and alkoxy with 1 to 6 carbon atoms, —$CF_3$, —OH, —$NH_2$, phenoxy, —$NR_1R_2$, —COOH, —CN, —SH, halogen, —$NO_2$, and COOR, particularly COO—$C_{1-6}$alkyl.

Compounds according to formula (1) can contain asymmetric centers at the carbon atoms marked thus: C*. Each of these carbon atoms can have an (R) or an (S) configuration, and preferably (S). In the preferred compounds the spiro carbon is (S) or (R) and the other asymmetric carbons are in the (S) configuration. Individual optical diastereoisomers as well as mixtures thereof are considered to be within the scope of this invention. The invention thus covers in particular (S,S,S,S) and (S,S,S,R) compounds and mixtures thereof; as well as (S,S,S) and (S,S,R) compounds and mixtures thereof. When diastereoisomeric products result from the synthetic procedures, the desired diastereoisomeric product can be separated by conventional chromatographic or fractional crystallization methods.

The compounds of formula (1) can be prepared by coupling compounds of formulas (2) and (3)

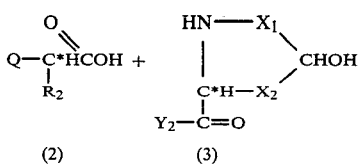

followed by oxidizing the >CHOH group to >C=O and reacting that product with compound (4)

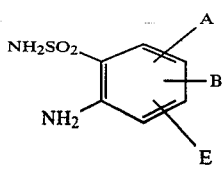

Both free —NH₂ groups react with the >C=O group to form the desired spiro linkage. The various substituents on compounds (2), (3) and (4) have been defined above.

It will be recognized by those skilled in this art that the coupling of compounds (2) and (3) can be carried out by conventional peptide linkage techniques, e.g. in the presence of a coupling agent such as DCC (N,N'-dicyclohexylcarbodiimide) or CDI (N,N'-carbonyldiimidazole). Alternatively, one may prefer to convert the —COOH group of compound (2) to —C(O)Cl, and then react the resulting intermediate with compound (3). Alternatively one may preferably convert the compound (2) to the corresponding N-carboxyanhydride (NCA) by allowing (2) to react with phosgene, and then react the resulting N-carboxyanhydride with compound (3) to yield the desired intermediate. One may alternatively prepare the spiro amino ester first by reacting (4) with the ketone derived from (3) via oxidation, and then reacting (2) with the resulting spiro amino ester in any of the above ways (NCA; acid chloride; or active ester-peptide coupling) to yield the desired intermediate. It will further be recognized that the nitrogen atom which is between the carbon atoms to which R₁ and R₂ are attached can be protected with a blocking group such as 2,2,2-trichloroethoxycarbonyl, or benzyloxycarbonyl. The protecting group is subsequently removed, preferably after compounds (2), (3) and (4) have been joined together. Other nitrogen atoms, in substituents such as NH₂(CH₂)₄—, should be protected and then deprotected in a similar manner. Similarly, Y₁ and Y₂ are preferably converted to ethoxy, t-butoxy, or benzyloxy, before the intermediates are reacted. If the free acid is desired, it is subsequently obtained by removal of the esterifying group in a known manner.

The compounds of the present invention in which one of Y₁ and Y₂ is —OH and the other is alkyl, such as methoxy or ethoxy, are preferably made by reacting compounds (2) and (3) as shown above in which one of Y₁ and Y₂ is the desired alkyl ester, and the other is an easily cleaved ester group such as t-butoxy. The amide intermediate thus prepared is oxidized and reacted with (4) to give the corresponding intermediate which upon a mild acid hydrolysis yields the desired monoester-monoacids.

When Q contains sulfur, the preferred synthetic route is via the acid chloride.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, H₂SO₄, H₃PO₄, as well as methanesulfonic, toluenesulfonic, maleic, acetic, malic, citric, fumaric and camphorsulfonic acids. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin -to- angiotensin I -to- angiotensin II sequence inhibit angiotensin I converting enzyme and therefore are useful in reducing or relieving hypertension.

Furthermore, the compounds within the scope of the present invention which possess diuretic activity promote relief from hypertension by promoting diuresis, and consequently have utility in treating congestive heart failure. Compounds within the scope of this invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE 1

A. 4-Hydroxy-L-Proline Ethyl Ester Hydrochloride

To a solution of N-Cbz-4-hydroxy-L-proline ethyl ester (3.29 g) in 40 ml ethanol was added 6 ml of ethanol saturated with gaseous HCl followed by 10% palladium on carbon (0.50 g). The mixture was hydrogenated on a Parr Hydrogenator at 30-40 psi for 3 hours. The solution was filtered over celite and concentrated in vacuo to provide 2.09 g of the crystalline product.

B. N-[N-[(1S)-1-(Ethoxycarbonyl)-3-phenylpropyl]-N-(2,2,2-trichloroethoxycarbonyl)-L-alanyl]-4-hydroxy-L-proline ethyl ester To N-[(1S)-1-(ethoxycarbonyl)-3-phenylpropyl]-N-(2,2,2-trichloroethoxycarbonyl)-L-alanine (5.94 g, 13.07 mmol) in 50 ml methylene chloride, under $N_2$, was added oxalyl chloride (5.70 ml, 65.33 mmol) and then N,N-dimethylformamide (20 uL). The solution was stirred 3.5 hours and concentrated in vacuo. The residue was diluted with 30 ml methylene chloride and cooled with an ice bath while under $N_2$. To this solution was added portionwise a mixture of 4-hydroxy-L-proline ethyl ester hydrochloride (1.96 g, 10.05 mmol) and triethylamine (6.99 ml, 50.25 mmol) in 40 ml methylene chloride. After the addition was complete the solution was slowly warmed to room temperature, stirred 18 hours and concentrated in vacuo. The residue was dissolved in ether and washed with water, 10% HCl, 1N NaOH, and brine, and dried (MgSO4) and concentrated in vacuo. Chromatography of the residue on HPLC, using 50% ethyl acetate in hexanes as eluents, provided 2.44 g (41%) of the oily product.

C. N-[N-[(1S)-1-(Ethoxycarbonyl)-3-phenylpropyl]-N-(2,2,2-trichloroethoxycarbonyl)-L-alanyl]-L-prolin-4-one ethyl ester To a solution of N-[N-[(1S)-1-(ethoxycarbonyl)-3-phenylpropyl]-N-(2,2,2-trichloroethoxycarbonyl)-L-alanyl]-4-hydroxy-L-proline ethyl ester (2.21 g, 3.71 mmol) in 30 ml methylene chloride was added pyridinium chlorochromate (PCC) (1.60 g, 7.43 mmol). The mixture was stirred 28 hours and additional PCC (1.60 g) was added. The mixture was stirred 72 hours and the solution was decanted from the solid residue. The residue was triturated with ether. The combined organic solutions were passed through a plug of silica gel. Concentration in vacuo of the filtrate provided 2.1 g (95%) of the oily product which was carried forward without further purification.

D. Spiro[(7-sulfonamyl-6-chloro-3,4-dihydro-2H-1,2,4-benzothiadiazine-1,1-dioxide)-3,4'-[N-[N-[(1S)-1-(ethoxycarbonyl)-3-phenylpropyl]-N-(2,2,2-trichloroethoxycarbonyl)-L-alanyl]-L-proline ethyl ester]]

To a solution of N-[N-[(1S)-1-(ethoxycarbonyl)-3-phenylpropyl]-N-(2,2,2-trichloroethoxycarbonyl)-L-alanyl]-L-prolin-4-one ethyl ester (1.01 g, 1.70 mmol) and 1-amino-3-chloro-4,6-benzenedisulfonamide (0.511 g, 1.79 mmol) in 15 ml ethanol was added 2 ml of ethanol saturated with gaseous HCl. The solution was heated to 65° C. for 1.5 hours and concentrated in vacuo. The residue was chromatographed on HPLC using 60% ethyl acetate in hexanes as eluents which provided the solid product.

E. Spiro[(7-sulfonamyl-6-chloro-3,4-dihydro-2H-1,2,4-benzothiadiazine-1,1-dioxide)-3,4'-[N-[N-[(1S)-1-(ethoxycarbonyl)-3-phenylpropyl]-L-alanyl]-L-proline ethyl ester]] hydrochloride To a solution of spiro[(7-sulfonamyl-6-chloro-3,4-dihydro-2H-1,2,4-benzothiadiazine-1,1-dioxide)-3,4'-[N-[N-[(1S)-1- (ethoxycarbonyl)-3-phenylpropyl]-N-(2,2,2-trichloroethoxycarbonyl)-L-alanyl]-L-proline ethyl ester]] (0.55 g) in 7 ml glacial acetic acid was added zinc dust (1.5 g). The mixture was stirred at room temperature for 1.1 hour, filtered over celite and gaseous HCl was added to the filtrate. The solution was concentrated in vacuo. The residue was triturated with 20% ethyl acetate in ether which provided the crystalline product, having the following structural formula:

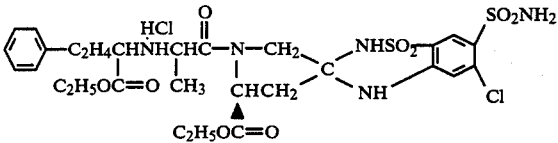

EXAMPLE 2

Spiro[(7-sulfonamyl-6-chloro-3,4-dihydro-2H-1,2,4-benzothiadiazine-1,1-dioxide)-3,4'-[N-[N-[(1S)-1-(hydroxycarbonyl)-3-phenylpropyl]-L-alanyl]-L-proline]]-hydrochloride To a solution of. spiro[(7-sulfonamyl-6-chloro-3,4-dihydro-2H-1,2,4-benzothiadiazine-1,1-dioxide)3,4'-[N-

[N-[(1S)-1-(ethoxycarbonyl)-3-phenylpropyl]-L-alanyl]-L-proline ethyl ester]] hydrochloride (0.60 g) in 5 ml ethanol was added aqueous sodium hydroxide (8.3 ml of a 1N solution). The solution stirred at room temperature for 20 hours, acidified to pH 1 with concentrated HCl and extracted with ethyl acetate. The organic layers were washed in brine, and dried (MgSO$_4$) and concentrated in vacuo. Trituration of the residue with 50% ethyl acetate in ether provided 0.51 g of the crystalline product m.p. 198° C. (dec.).

The following compounds, which are within the scope of this invention, are made by the procedures employed in Examples 1–2:

EXAMPLE 3

Spiro [(7-sulfonamyl-6-chloro-3, 4-dihydro-2H-1, 2,4-benzothiadiazine-1, 1-dioxide)-3, 4'-[N-[N-[(1S)-1-(ethoxycarbonyl)-3-phenylpropyl]-L-alanyl]-L-proline]] hydrochloride (referring to formula (1): a=d=y=1, x=0).

EXAMPLE 4

Spiro [(7-sulfonamyl-6-chloro-3, 4-dihydro-2H-1, 2,4-benzothiadiazine-1, 1-dioxide)-3, 4'-[N-[N-α(1S)-1-(hydroxycarbonyl)-3-phenylpropyl]-L-lysyl]-L-proline]] dihydrochloride (formula (1): a=d=y=1, x=0).

EXAMPLE 5

Spiro [(7-sulfonamyl-6-chloro-3, 4-dihydro-2H-1, 2, 4-benzothiadiazine-1, 1-dioxide)-3, 4'-[N-[N-[(1S)-1-(ethoxycarbonyl)-3-phenylpropyl]-L-valyl]-L-proline]] hydrochloride (formula (1): a=d=1=y-1, x=0).

EXAMPLE 6

Spiro[(7-sulfonamyl-6-chloro-3, 4-dihydro-2H-1, 2, 4-benzothiadiazine-1, 1-dioxide)-3, 4'-[N-[N-[(1S)-1-(hydroxycarbonyl)-3-phenylpropyl]-L-phenylalanyl]-L-proline]] hydrochloride (formula (1): a=d=y=1; x=0.

EXAMPLE 7

Spiro[(7-sulfonamyl-6-chloro-3, 4-dihydro-2H-1, 2, 4-benzothiadiazine-1, 1-dioxide)-3, 4'-[N-[N-[(1S)-1-(hydroxycarbonyl)-3-methylbutyl]-L-alanyl]-L-proline]] hydrochloride (formula (1): a=d=y=1, x=O).

EXAMPLE 8

Spiro [(7-sulfonamyl-6-chloro-3, 4-dihydro-2H-1, 2, 4-benzothiadiazine-1, 1-dioxide)-3, 4'-[N-[N-[(1S)-1-(ethoxycarbonyl)-1-(2,3-dihydro-1H-inden-2-yl) methyl]-L-alanyl]-L-proline]] hydrochloride (formula (1): a=d=y=1; X=0).

EXAMPLE 9

Spiro [(7-sulfonamyl-6-chloro-3, 4-dihydro-2H-1, 2, 4-benzothiadiazine-1, 1-dioxide)-3, 4'-[N-[N-[(1S)-1-(ethoxycarbonyl)-3- phenylpropyl]-L-alanyl]-L-pipecolinic acid]] hydrochloride (formula (1): a=2, d=y=1, x=0).

EXAMPLE 10

Spiro[(7-sulfonamyl-6-chloro-3, 4-dihydro-2H-1, 2, 4-benzothiadiazine-1, 1-dioxide)-3, 5'-[N-[N-[(1S)-1-(ethoxycarbonyl)-3-phenylpropyl]-L-alanyl-L-pipecolinic acid]] hydrochloride (formula (1): d=2, a=y=1, x=0).

EXAMPLE 11

Spiro[(7-sulfonamyl-6-chloro-3, 4-dihydro-2H-1, 2, 4-benzothiadiazine-1, 1-dioxide)-3, 4'-[N-[N α-[(1S)-1-(hydroxycarbonyl)-3-phenylpropyl]-L-lysyl]- L-pipecolinic acid]] dihydrochloride (formula (1): a=2, d=y=1, x=0).

EXAMPLE 12

Spiro[(7-sulfonamyl-6-chloro-3, 4-dihydro-2H-1, 2, 4-benzothiadiazine-1, 1-dioxide)-3, 5'-[N-[N-[(1S)-1-(ethoxycarbonyl)-3-phenylpropyl)-L-alanyl]- L-homopipecolinic acid ]] hydrochloride- (formula (1): a=d=2, y=1, x=0).

EXAMPLE 13

Spiro[(7-sulfonamyl-6-chloro-3, 4-dihydro-2H-1, 2, 4-benzothiadiazine-1, 1-dioxide)-3, 4'-[N-[N-α-[(1S)-1-(hydroxycarbonyl)-3-phenylpropyl]-L-lysyl]-L-homopipecolinic acid]] dihydrochloride (formula (1): a=3, d=y=1, x=0).

EXAMPLE 14

Spiro[(7-sulfonamyl-6-chloro-3, 4-dihydro-2H-1, 2, 4-benzothiadiazine-1, 1-dioxide-3, 4'-[N-[N-[(1S)-1-(hydroxycarbonyl)-1- (2,3-dihydro-1H-inden-2-yl)methyl]-L-alanyl]-L-homopipecolinic acid]] hydrochloride (formula (1): a=3, d=y=1, x=0).

EXAMPLE 15

Spiro [(7-sulfonamyl-6-chloro-3, 4-dihydro-2H-1, 2, 4-benzothiadiazine-1, 1-dioxide)-3, 4'-[N-(3-mercapto-2-methylpropanoyl)-L-proline]] (formula (1): a=d=y=1, x=0).

EXAMPLE 16

Spiro (7-sulfonamyl-6-chloro-3, 4-dihydro-2H-1, 2, 4-benzothiadiazine-1, 1-dioxide)-3, 4'-[N-(3-trimethylacetylthio-2- methylpropanoyl)-L-proline]] (formula (1): a=d=y=1, x=0).

What is claimed is:

1. A compound of the formula

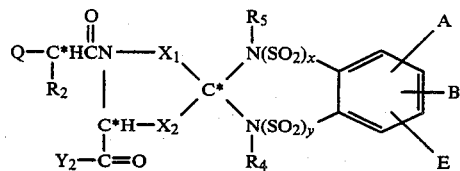

wherein

Q is $Y_1$—C(O)—C*H($R_1$)—NH—,—NH$_2$, $R_1$—C(O)—S—(C*H($R_1$))$_{0-1}$—, or HS—(C*H($R_1$))$_{0-1}$—;

$Y_1$ and $Y_2$ are independently —OH, —OR, or —NR$_1$R$_2$;

one of x and y is 1 and the other is 0;

R, $R_1$, $R_2$, $R_4$ and $R_5$ are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an alkyl group having 1 to 6 carbon atoms which is substituted with —NH$_2$, [—NH—C(NH$_2$)=NH$_2$]—$^{N-}$

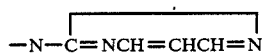

A, B and E are independently hydrogen, halogen, hydroxy, —CF$_3$, —OR, —NR$^1$R$_2$, —C(O)Y$_1$, —SO$_2$R, or —SO$_2$NR$_1$R$_2$ provided that at least two of A, B and E are not hydrogen;

X$_1$ is —(CH$_2$)$_a$—, —(CH$_2$)$_b$S(CH$_2$)$_c$—, —(CH$_2$)$_b$C(O)(CH$_2$)$_c$—, or —(CH$_2$)$_b$CH(R$_3$)(CH$_2$)$_c$—;

X$_2$ is —(CH$_2$)$_d$—, —(CH$_2$)$_e$S(CH$_2$)$_f$—, —(CH$_2$)$_e$C(O)(CH$_2$)$_f$—, or —(CH$_2$)$_e$CH(R$_3$)(CH$_2$)$_f$—;

provided that a is 0-4, b is 0-3, c is 0-3, d is 0-4, e is 0-3, f is 0-3, (a+d) is 2-4, (a+e+f) is 1-3, (b+c+d) is 1-3, and (b+c+e+f) is 0-2; and R$_3$ is hydroxy, phenyl, alkyl having 1 to 6 carbon atoms, or alkoxy having 1 to 6 carbon atoms;

wherein the alkyl, cycloalkyl, aryl, and fused aryl-cycloalkyl groups may carry substituents selected from the group consisting of alkoxy with 1 to 6 carbon atoms, —CF$_3$, —OH, —SH, halogen, —NO$_2$, and —COOR; and pharmaceutically acceptable acid addition, alkali metal, and alkaline earth metal salts thereof.

2. A compound or salt according to claim 1 wherein the spiro carbon atom is in the (S) or (R) configuration and the other unsymmetrical carbon atoms are in the (S) configuration.

3. A compound or salt according to claim 1 wherein R$_4$, R$_5$, and E are hydrogen.

4. A compound or salt according to claim 3 wherein X$_1$ is —(CH$_2$)$_a$—and X$_2$ is —(CH$_2$)$_d$—.

5. A compound or salt according to claim 4 wherein Y$_1$ and Y$_2$ are independently —OH or alkoxy having 1 to 8 carbon atoms.

6. A compound or salt according to claim 5 wherein R$_1$ is hydrogen, alkyl, aryl, aryl-alkyl, or fused arylcycloalkyl; and R$_2$ is hydrogen, alkyl, aryl, aryl-alkyl, fused aryl-cycloalkyl, or amino-substituted alkyl.

7. The compound according to claim 6 which is Spiro[(7-sulfonamyl-6-chloro-3, 4-dihydro-2H-1, 2, 4-benzothiadiazine-1, 1-dioxide)-3, 4'-[N-[N-[(1S)-1-(ethoxycarbonyl)-3-phenylpropyl]-L-alanyl]-L-proline]] and its pharmaceutically acceptable acid addition, alkali metal, and alkaline earth metal salts.

8. The compound according to claim 6 which is Spiro[(7-sulfonamyl-6-chloro-3, 4-dihydro-2H-1, 2, 4-benzothiadiazine-1, 1-dioxide)-3, 4'-[N-[N-α-[(1S)-1-(hydroxycarbonyl)-3-phenylpropyl]-L-lysyl]-L-proline]] and its pharmaceutically acceptable acid addition, alkali metal, and alkaline earth metal salts.

9. The compound according to claim 6 which is Spiro[(7-sulfonamyl-6-chloro-3, 4-dihydro-2H-1, 2, 4-benzothiadiazine-1, 1-dioxide)-3, 4'-[N-[N-[(1S)-1-(ethoxycarbonyl)-3-phenylpropyl]-L-valyl]-L-proline]] and its pharmaceutically acceptable acid addition, alkali metal, and alkaline earth metal salts.

10. The compound according to claim 6 which is Spiro[(7-sulfonamyl-6-chloro-3, 4-dihydro-2H-1, 2, 4-benzothiadiazine-1, 1-dioxide)-3, 4'-[N-[N-[(1S)-1-(hydroxycarbonyl)-3-phenylpropyl]-L-phenylalanyl]-L-proline]] and its pharmaceutically acceptable acid addition, alkali metal, and alkaline earth metal salts.

11. The compound according to claim 6 which is Spiro[(7-sulfonamyl-6-chloro-3, 4-dihydro-2H-1, 2, 4-benzothiadiazine-1, 1-dioxide)-3, 4'-[N-[N-[(1S)-1-(hydroxycarbonyl)-3-methylbutyl]-L-alanyl]-L-proline]] and its pharmaceutically acceptable acid addition, alkali metal, and alkaline earth metal salts.

12. The compound according to claim 6 which is Spiro[(7-sulfonamyl-6 chloro-3, 4-dihydro-2H-1, 2, 4-benzothiadiazine-1, 1-dioxide)-3, 4'-[N-[N-[(1S)-1-(ethoxycarbonyl)- 1-(2,3-dihydro-1H- inden-2-yl) methyl]L-alanyl]-L-proline]] and its pharmaceutically acceptable acid addition, alkali metal, and alkaline earth metal salts.

13. The compound according to claim 6 which is Spiro[(7-sulfonamyl-6-chloro-3, 4-dihydro-2H-1,2, 4-benzothiadiazine-1, 1-dioxide)-3, 4'-[N-[N-[(1S)-1-(ethoxycarbonyl)-3-phenylpropyl]-L-alanyl]-L-pipecolinic acid]] and its pharmaceutically acceptable acid addition, alkali metal, and alkaline earth metal salts.

14. The compound according to claim 6 which is Spiro[(7-sulfonamyl-6-chloro-3, 4-dihydro-2H-1, 2, 4-benzothiadia-zine-1, 1-dioxide)-3, -5'-[N-[N-[(1S)-1-(ethoxycarbonyl)-3-phenylpropyl]-L-alanyl]-L-pipecolinic acid]] and its pharmaceutically acceptable acid addition, alkali metal, and alkaline earth metal salts.

15. The compound according to claim 6 which is Spiro[(7-sulfonamyl-6-chloro-3, 4-dihydro-2H-1, 2, 4-benzothiadia-zine-1, 1-dioxide)-3, 4'-[N-[Nα-[(1S)- 1-(hydroxycarbonyl)-3-phenylpropyl]-L-lysyl]- L-pipecolinic acid]] and its pharmaceutically acceptable acid addition, alkali metal, and alkaline earth metal salts.

16. The compound according to claim 6 which is Spiro[(7-sulfonamyl-6-chloro-3, 4-dihydro-2H-1, 2, 4-benzothiadiazine-1, 1-dioxide)-3, 5'-[N-[N-[(1S)- 1-(ethoxycarbonyl)-3-phenylpropyl]-L-alanyl]- L-homopipecolinic acid]] and its pharmaceutically acceptable acid addition, alkali metal, and alkaline earth metal salts.

17. The compound according to claim 6 which is Spiro[(7-sulfonamyl-6-chloro-3, 4-dihydro-2H-1, 2, 4-benzothiadiazine- 1, 1-dioxide)-3, 4'-[N-[N-α-[(1S)-1-(hydroxycarbonyl)-3-phenylpropyl]-L-lysyl]-L-homopipecolinic acid]] and its pharmaceutically acceptable acid addition, alkali metal, and alkaline earth metal salts.

18. The compound according to claim 6 which is Spiro[(7-sulfonamyl-6-chloro-3, 4-dihydro-2H-1, 2, 4-benzothiadiazine-1, 1-dioxide-3, 4'-[N-[N-[(1S)- 1-(hydroxycarbonyl)-1-(2,3-dihydro-1H-inden-2-yl)methyl]-L-alanyl]-L-homopipecolinic acid]] and its pharmaceutically acceptable acid addition, alkali metal, and alkaline earth metal salts.

19. The compound according to claim 6 which is Spiro[(7-sulfonamyl-6-chloro-3, 4-dihydro-2H-1, 2, 4-benzothiadiazine-1, 1-dioxide)-3, 4'-[N-(3-mercapto-2-methylpropanoyl)-L-proline]] and its pharmaceutically acceptable acid addition, alkali metal, and alkaline earth metal salts.

20. The compound according to claim 6 which is Spiro(7-sulfonamyl-6-chloro-3, 4-dihydro-2H-1, 2, 4-benzothiadiazine-1, 1-dioxide)-3, 4'-[N-(3-trimethyl acetylthio-2- methylpropanoyl)-L-proline]] and its pharmaceutically acceptable acid addition, alkali metal, and alkaline earth metal salts.

21. A pharmaceutical preparation comprising an antihypertensive effective amount of a compound or salt according to claim 1, in association with a pharmaceutically acceptable carrier.

22. A method of alleviating hypertension in a host suffering therefrom comprising administering to said host an antihypertensive effective amount of a compound or salt according to claim 1.

23. The compound according to claim 6 which is spiro[7-sulfonamyl-6-chloro-3, 4-dihydro-2H-1,2, 4-benzothiadiazine-1, 1-dioxide)-3, 4'[-N-[N-[(1S)-1-(hydroxycarbonyl)-3-phenylpropyl]-L-alanyl]-L-proline]] and its pharmaceutically acceptable acid addition, alkali metal, and akaline earth metal salts.

* * * * *